(12) United States Patent
Morimoto

(10) Patent No.: US 10,485,411 B2
(45) Date of Patent: Nov. 26, 2019

(54) ENDOSCOPE

(71) Applicant: FUJIFILM Corporation, Tokyo (JP)

(72) Inventor: Yasuhiko Morimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 429 days.

(21) Appl. No.: 15/345,475

(22) Filed: Nov. 7, 2016

(65) Prior Publication Data

US 2017/0127920 A1    May 11, 2017

(30) Foreign Application Priority Data

Nov. 9, 2015  (JP) .................................. 2015-219352

(51) Int. Cl.
*A61B 1/00* (2006.01)
*A61B 1/018* (2006.01)
*A61B 8/12* (2006.01)
*A61B 8/00* (2006.01)

(52) U.S. Cl.
CPC ................ *A61B 1/018* (2013.01); *A61B 8/12* (2013.01); *A61B 8/445* (2013.01); *A61B 8/4494* (2013.01)

(58) Field of Classification Search
CPC . A61B 1/018; A61B 1/00128; A61B 1/00119; A61B 1/00098
USPC .................................................. 600/127, 140
See application file for complete search history.

(56) References Cited

U.S. PATENT DOCUMENTS

| | | | |
|---|---|---|---|
| 5,735,793 A * | 4/1998 | Takahashi | A61B 1/00059 600/104 |
| 2011/0208001 A1 * | 8/2011 | Haeckl | A61B 1/00071 600/125 |
| 2016/0367231 A1 * | 12/2016 | Uemichi | A61B 8/0841 |

FOREIGN PATENT DOCUMENTS

| | | |
|---|---|---|
| JP | S56163405 | 12/1981 |
| JP | H02021852 | 1/1990 |
| JP | 2002209829 | 7/2002 |
| JP | 2002209829 A * | 7/2002 |

OTHER PUBLICATIONS

"Search Report of Euorpe Counterpart Application", dated Apr. 11, 2017, p. 1-p. 5.
"Office Action of Japan Counterpart Application," dated Oct. 30, 2018, with English translation thereof, p. 1-p. 6.

* cited by examiner

*Primary Examiner* — Alexandra L Newton
(74) *Attorney, Agent, or Firm* — JCIPRNET

(57) ABSTRACT

A fixing sleeve that is fitted outward on a connecting portion between a connecting pipe and a treatment tool inserting tube for fixation of the connecting portion comprises a cylindrical sleeve body, an arc-shaped portion that is connected to a proximal end side of the sleeve body, is formed to be coaxial with a sleeve center axis of the sleeve body and has a center angle smaller than 180°, and a projection portion that is formed along a peripheral direction of the sleeve center axis on an inner peripheral surface in the arc-shaped portion in a radial inside of the sleeve center axis. A part of the treatment tool inserting tube is flexibly deformed in a convex shape by the projection portion, and the part thereof is supported by the projection portion.

24 Claims, 15 Drawing Sheets

ENDOSCOPE

CROSS-REFERENCE TO RELATED APPLICATIONS

The present application claims priority under 35 U.S.C. § 119 to Japanese Patent Application No. 2015-219352, filed on Nov. 9, 2015. The above application is hereby expressly incorporated by reference, in its entirety, into the present application.

BACKGROUND OF THE INVENTION

Field of the Invention

The present invention relates to endoscopes, and particularly, to an endoscope in which a treatment tool inserting tube and a connecting pipe, in which a treatment tool is inserted, are fixed through a fixing sleeve.

Description of the Related Art

Conventionally a medical diagnosis using an endoscope is widely made in medical fields. Particularly an imaging element of a charge-coupled device (CCD) or the like is built into a distal end rigid portion of an insertion portion in the endoscope inserted into a body to take an image in the body. The image is subjected to signal processing in a processor device to be displayed on a monitor. A doctor observes the image to make a diagnosis or insert a treatment tool from a treatment tool inserting port and perform treatment such as collection of samples or removal of polyps.

The endoscope is provided with an operating unit that is grasped by a practitioner to be operated and an insertion portion a proximal end of which is connected to the operating unit to be inserted into the body, wherein a proximal end of a universal cable is connected to the operating unit. A connector in a distal end of the universal cable is removably connected to an optical source device or a processor device, thereby making the endoscope become in a usable state.

In such an endoscope, there has been recently used the treatment tool that is large in size and is high in bending stiffness. The treatment tool is inserted into the insertion portion from the treatment tool inserting port provided in the operating unit of the endoscope and is led out to an exterior from a treatment tool leading-out port provided in the distal end rigid portion of the endoscope.

A proximal end of a treatment tool inserting tube (called a forceps tube as well) having flexibility is connected to the treatment tool inserting port, the treatment tool inserting tube is disposed from a flexible portion to a curved portion of the insertion portion, and a distal end of the treatment tool inserting tube is fitted outward on a proximal end of a metallic connecting pipe (called a forceps pipe as well) (for example, refer to Japanese Patent Application Publication No. 02-021852 or Japanese Patent Application Publication No. 2002-209829). Thereby the treatment tool inserting tube and the connecting pipe are connected to cause the distal end of the connecting pipe to be communicated with the treatment tool leading-out port of the distal end rigid portion.

In a state where a puncture needle as the treatment tool is inserted into a flexible sheath, the puncture needle is inserted with the sheath from the treatment tool inserting port and is led out from the treatment tool leading-out port through the treatment tool inserting tube and the connecting pipe. The bending stiffness of the sheath is lower than the bending stiffness of the puncture needle, but is controlled by the bending stiffness of the puncture needle following the insertion of the puncture needle. In a case of the puncture needle, the puncture needle with the sheath is called the treatment tool.

SUMMARY OF THE INVENTION

Incidentally the ultrasonic endoscope disclosed in Japanese Patent Application Publication No. 02-021852 has a problem as follows in a case of inserting the puncture needle for aspiration biopsy in a state where the insertion portion is curved toward an up-side (top side), that is, in a so-called up-angle form. The up-angle form is a state where the insertion portion is curved to an up-side where a direction vertical to a center axis of the insertion portion which is a direction of extracting the treatment tool by an ultrasonic vibrator is the up-side.

FIG. 14 is an essential-portion enlarging cross section illustrating a state where a puncture needle 100 of a high bending stiffness with a sheath 102 is inserted into a treatment tool inserting tube 104 in the up-angle form. As illustrated in this drawing, a connecting pipe 106 and the treatment tool inserting tube 104 are connected such that there occurs no difference in level therebetween due to an inner diameter difference between an inner peripheral surface 104A of the treatment tool inserting tube 104 and an inner peripheral surface 106A of the connecting pipe 106, but there are some cases where at the up-angle form, a distal end 102A of the sheath 102 knocks on a proximal end 106B of the connecting pipe 106 to make it difficult to move forward the sheath 102 to the connecting pipe 106 from that position.

Japanese Patent Application Publication No. 2002-209829 discloses a pipe connecting structure for connecting the treatment tool inserting tube and the connecting pipe.

That is, as the essential-portion enlarging cross section in a non-angle form illustrated in FIG. 15A, the distal end side of the treatment tool inserting tube 104 is fitted outward on the proximal end side of the connecting pipe 106, and a stainless fixing sleeve 108 is fitted outward on the distal end side of the treatment tool inserting tube 104. Thereby a connecting portion between the treatment tool inserting tube 104 and the connecting pipe 106 is fixed.

A part 104B of the treatment tool inserting tube 104 positioned in the connecting portion is supported from outside by an adhesive 110 filled between an inner peripheral surface of the fixing sleeve 108 and an outer peripheral surface of the treatment tool inserting tube 104.

FIG. 15B is an essential-portion enlarging cross section illustrating the up-angle form changed from the non-angle form in FIG. 15A, wherein the puncture needle 100 is inserted with the sheath 102 in the treatment tool inserting tube 104. As illustrated in FIG. 15B, even in the endoscope in Japanese Patent Application Publication No. 2002-209829, a part 104B of the treatment tool inserting tube 104 abutting on the distal end 102A of the sheath 102 is pressed by the distal end 102A of the sheath 102 to be easily flexibly deformed in a diameter-increasing direction indicated as an arrow "b". Therefore there occurs a defect that the distal end 102A of the sheath 102 knocks on the proximal end 106B of the connecting pipe 106.

This defect is not limited to the sheath 102, but likewise, occurs at the time of inserting the other treatment tool such as the forceps having a high bending stiffness.

The present invention is made in view of the foregoing problems, and an object of the present invention is to provide an endoscope that can smoothly move forward a treatment tool toward a connecting pipe from a treatment tool inserting tube in an up-angle form.

For achieving the object of the present invention, an endoscope according to the present invention comprises an insertion portion to be inserted into a body, a distal end portion body provided in a distal end of the insertion portion, a treatment tool leading-out port formed in the distal end portion body, a connecting pipe that is mounted on the distal end portion body, a distal end of which is communicated with the treatment tool leading-out port, a treatment tool inserting tube having flexibility that is arranged in the insertion portion, a distal end of which is connected to the connecting pipe, and a fixing sleeve that is fitted outward on a connecting portion between the connecting pipe and the treatment tool inserting tube for fixation of the connecting portion, wherein the fixing sleeve comprises a cylindrical sleeve body having a distal end, a proximal end and a sleeve center axis, an arc-shaped portion that is connected to a proximal end side of the sleeve body, is formed in an arc shape along a cylindrical surface of the sleeve body and has a center angle smaller than 180°, and a projection portion that is formed along a peripheral direction of the sleeve center axis on an inner peripheral surface of the arc-shaped portion in a radial inside of the sleeve center axis.

According to the present invention, the part of the treatment tool inserting tube positioned in the connecting pipe between the connecting pipe and the treatment tool inserting tube is pressed in the radial inside of the sleeve center axis by the projection portion formed in the arc-shaped portion of the fixing sleeve to be flexibly deformed in a convex shape. The difference in level due to the inner diameter difference between the connecting pipe and the treatment tool inserting tube is eliminated or alleviated by a part of the treatment tool inserting tube flexibly deformed in the convex shape.

In this endoscope, even if the treatment tool is inserted in the up-angle form and the distal end of the treatment tool abuts on the part of the treatment tool inserting tube flexibly deformed in the convex shape, since the part of the convex portion is supported by the projection portion of the fixing sleeve to suppress the flexible deformation, the difference in level does not occur again. Thereby, according to one aspect of the present invention, even if the treatment tool is inserted in the up-angle form, since the distal end of the treatment tool does not knock on the proximal end of the connecting pipe, it is possible to smoothly move forward the treatment tool from the treatment tool inserting tube toward the connecting pipe.

In view of fitting the fixing sleeve outward on the treatment tool inserting tube to fix the connecting portion, it is preferable that an inner diameter of the fixing sleeve is equal to or slightly larger than an outer diameter of the treatment tool inserting tube. The fixing sleeve is provided with the projection portion on the inner peripheral surface of the arc-shaped portion, but the arc-shaped portion is formed in an arc shape along a cylindrical surface of the sleeve body and has the center angle that is set within a range smaller than 180°. Therefore the arc-shaped portion does not give an influence on an effective inner diameter of the fixing sleeve. Since the arc-shaped portion does not give the influence on the effective inner diameter of the fixing sleeve, it is possible to insert the treatment tool inserting tube inside of the fixing sleeve without deformation of the treatment tool inserting tube.

Further, it is preferable that the projection portion is disposed in a position close to the proximal end side of the sleeve body for eliminating or alleviating the difference in level, but when the projection portion is disposed too closely, the effective inner diameter of the fixing sleeve is apparently smaller than the outer diameter of the treatment tool inserting tube because of the presence of the projection portion. For this reason, the projection portion is arranged in the arc-shaped portion connected to the proximal end side of the sleeve body, which does not give an influence on the effective inner diameter of the fixing sleeve.

According to one aspect of the present invention, it is preferable that the arc-shaped portion is coaxial with the sleeve center axis.

According to one aspect of the present invention, it is preferable that when a curvature radius of the projection portion is indicated as "r" and an inner diameter of the connecting pipe is indicated as "D", the following formula "r">D/2 is met.

According to the one aspect of the present invention, since it is possible to suppress an extension amount of a part of the treatment tool inserting tube flexibly deformed in the convex shape, it is possible to smoothly move forward the treatment tool from the treatment tool inserting tube toward the connecting pipe without interruption of the part flexibly deformed in the convex shape.

According to one aspect of the present invention, it is preferable that when a curvature radius of the projection portion is indicated as "r" and an outer diameter of the treatment tool inserting tube is indicated as "D2", the following formula "r"<D2/2 is met.

According to one aspect of the present invention, it is preferable that the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

According to one aspect of the present invention, it is preferable that the projection portion includes a second inclined surface that is provided in a proximal end side of the sleeve center axis and has a normal direction including a component in a direction toward the proximal end side in a direction of the sleeve center axis and a component in a direction toward a radial inside of the sleeve center axis.

According to one aspect of the present invention, it is preferable that the projection portion is formed in a trapezoidal shape in a cross-section surface including the sleeve center axis, the shape having a width smaller toward a radial inside of the sleeve center axis.

According to one aspect of the present invention, it is preferable that the projection portion is formed in a curved surface shape in a cross-section surface including the sleeve center axis, the shape having an edge portion without corners.

According to one aspect of the present invention, it is preferable that the projection portion of the arc-shaped portion includes an inclined surface in at least one surface of the proximal end side and the distal end side.

Upon fixing the connecting portion between the connecting pipe and the treatment tool inserting tube by the fixing sleeve, a fixing operation of causing the fixing sleeve in which the treatment tool inserting tube is inserted to slide in the distal end side toward the connecting pipe is performed. It is possible to alleviate a fixing operation force at this moment by the first inclined surface in the distal end side of the projection portion. Therefore it is possible to prevent damage of the treatment tool inserting tube due to the fixing operation force of the fixing sleeve.

On the other hand, by providing the second inclined surface in the proximal end side of the projection portion, upon pressing the part of the treatment tool inserting tube by the distal end of the treatment tool, the pressing force can be alleviated by the second inclined surface. Accordingly it is possible to prevent the damage of the treatment tool inserting tube due to the pressing force of the treatment tool.

When the shape of the projection portion is the trapezoidal shape, it is possible to provide the inclined surface in each of the proximal end side and the distal end side of the projection portion. The shape of the projection portion may be a curved surface shape composed of a curved surface with an edge portion.

According to one aspect of the present invention, it is preferable that, as viewed in a lateral side vertical to a body center axis of the distal end portion body, a pipe center axis of the connecting pipe is obliquely-crossed to the body center axis of the distal end portion body, and a normal direction toward the center of the arc-shaped portion includes a component in a direction toward the proximal end side of the body center axis in the distal end portion body.

According to the one aspect of the present invention, in the endoscope in the form where the pipe center axis of the connecting pipe is arranged to be obliquely-crossed to the body center axis of the distal end portion body, the normal direction toward the center of the arc-shaped portion includes the component in the direction toward the proximal end side of the body center axis in the distal end portion body. Therefore it is possible to flexibly deform in the convex shape a part of the treatment tool inserting tube on which the distal end of the treatment tool inserted into the treatment tool inserting tube abuts to eliminate or alleviate the difference in level due to the inner diameter difference between the connecting pipe and the treatment tool inserting tube. Accordingly it is possible to smoothly move forward the treatment tool toward the connecting pipe from the treatment tool inserting tube in the up-angle form.

The pipe center axis is obliquely-crossed to the body center axis, but the concept of the oblique crossing includes a state where the pipe center axis is three-dimensionally crossed to the body center axis as viewed from the body center axis of the distal end portion body.

According to one aspect of the present invention, it is preferable that the treatment tool inserting tube includes a distal end-side tube portion connected to the connecting pipe, and a proximal end-side tube portion that is connected to a proximal end side of the distal end-side tube portion and is provided in a position eccentric from the pipe center axis of the connecting pipe, and the arc-shaped portion is provided at the opposite side to a tube center axis of the proximal end-side tube portion to the pipe center axis of the connecting pipe.

According to the one aspect of the present invention, in the endoscope in the form where the tube center axis of the proximal end-side tube portion is arranged to be eccentric to the pipe center axis of the connecting pipe, the arc-shaped portion is provided at the opposite side to the tube center axis of the proximal end-side tube portion to the pipe center axis of the connecting pipe. Therefore it is possible to flexibly deform in the convex shape a part of the treatment tool inserting tube on which the distal end of the treatment tool inserted into the treatment tool inserting tube abuts to eliminate or alleviate the difference in level due to the inner diameter difference between the connecting pipe and the treatment tool inserting tube. Accordingly it is possible to smoothly move forward the treatment tool toward the connecting pipe from the treatment tool inserting tube in the up-angle form.

According to the endoscope of the present invention, it is possible to smoothly move forward the treatment tool toward the connecting pipe from the treatment tool inserting tube in the up-angle form.

DETAILED DESCRIPTION OF THE PREFERRED EMBODIMENTS

Hereinafter, preferred embodiments of endoscopes according to the present invention will be in detail described with reference to the accompanying drawings.

Figure 1:
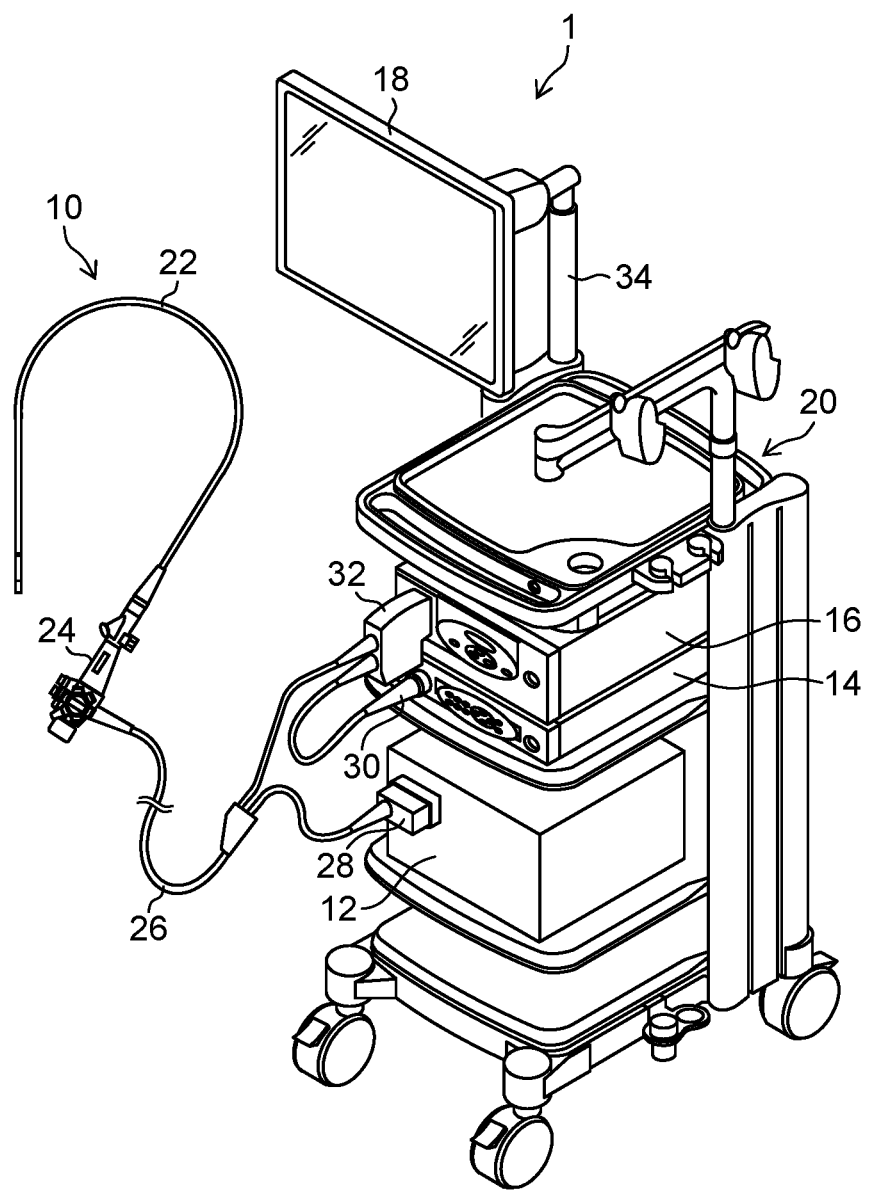
FIG. 1 is an entire configuration diagram of an ultrasonic examination system including an ultrasonic endoscope in the present embodiment.
Figure 2:
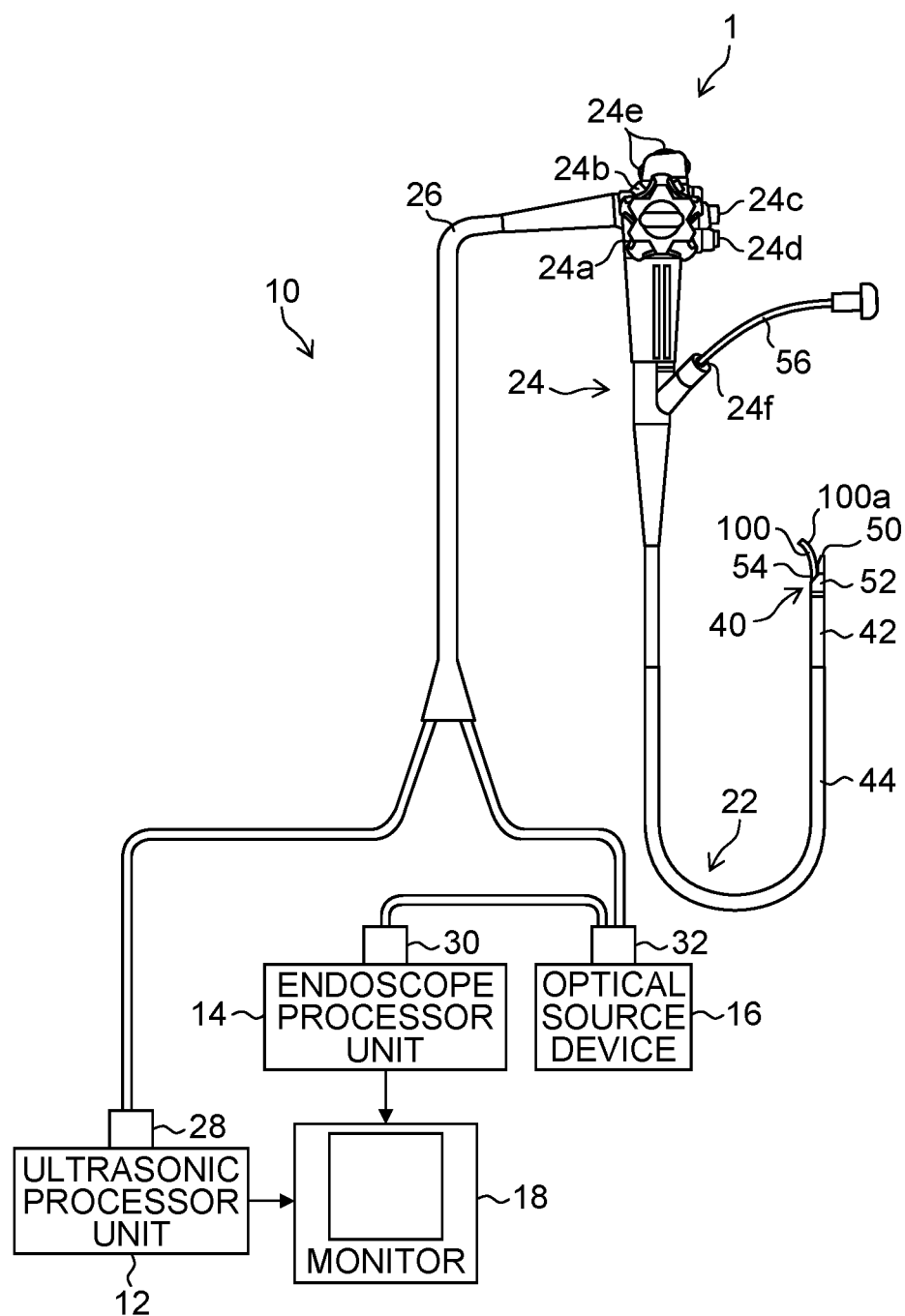
FIG. 2 is a block diagram illustrating an entire configuration of the ultrasonic examination system in FIG. 1.

FIG. 1 is an entire configuration diagram of an ultrasonic examination system 1 including an ultrasonic endoscope 10 to which an endoscope in the present embodiment is applied. FIG. 2 is a block diagram illustrating an entire configuration of the ultrasonic examination system 1 in FIG. 1.

[Ultrasonic Examination System 1]

The ultrasonic examination system 1 includes the ultrasonic endoscope 10 that takes an endoscope image and an ultrasonic image in the body, an ultrasonic processor unit 12 that generates the ultrasonic image, an endoscope processor unit 14 that generates the endoscope image, an optical source device 16 that supplies illumination light for illuminating the inside of the body to the ultrasonic endoscope 10, and a monitor 18 that displays the endoscope image and the ultrasonic image.

[Ultrasonic Endoscope 10]

The ultrasonic endoscope 10 is a convex type ultrasonic endoscope, and includes an insertion portion 22 to be inserted into a body, an operating unit 24 provided to be connected to a proximal end of the insertion portion 22, and a universal cord 26 a proximal end of which is connected to the operating unit 24. A connector 28 connected to the ultrasonic processor unit 12, a connector 30 connected to the endoscope processor unit 14 and a connector 32 connected to the optical source device 16 are provided in a distal end of the universal cord 26. The ultrasonic endoscope 10 is removably connected to the ultrasonic processor unit 12, the endoscope processor unit 14 and the optical source device 16 through the respective connectors 28, 30, 32.

The ultrasonic processor unit 12, the endoscope processor unit 14 and the optical source device 16 are loaded on a cart 20 with a caster as illustrated in FIG. 1 to move integrally. The monitor 18 is attached to a support rod 34 of the cart 20, and is adjusted in direction and height of the screen by an unillustrated rotational mechanism and an unillustrated height adjusting mechanism provided in the support rod 34.

<Insertion Portion 22>

As illustrated in FIG. 2, the insertion portion 22 includes a distal end rigid portion 40 having a distal end portion body 70 (refer to FIG. 3) formed of a rigid material, a curved portion 42 provided to be connected to a proximal end side of the distal end rigid portion 40, and a flexible portion 44 that connects a proximal end side of the curved portion 42 and a distal end side of the operating unit 24 and has flexibility in a thin diameter and in an elongated shape. That is, the distal end portion body 70 is provided in the distal end of the insertion portion 22. An after-mentioned treatment tool leading-out port 54 is formed in the distal end portion body 70 (refer to FIG. 3).

Figure 3:
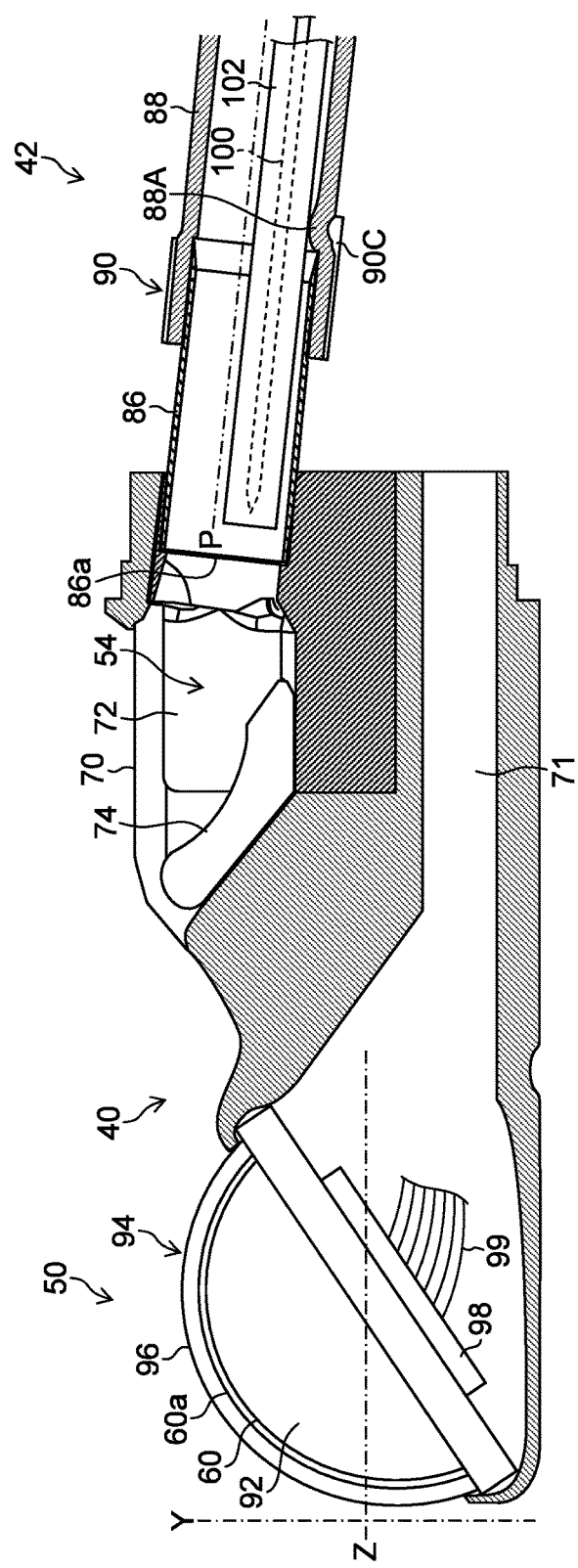
FIG. 3 is an essential-portion enlarging cross section illustrating a non-angle form of an insertion portion in the ultrasonic endoscope illustrated in FIG. 1.

FIG. 3 is an essential-portion enlarging cross section illustrating the non-angle form of the insertion portion 22 in the ultrasonic endoscope 10 illustrated in FIG. 1.

A treatment tool inserting tube 88 is arranged inside the insertion portion 22 to guide the treatment tool in which the puncture needle 100 is inserted into the sheath 102 to the treatment tool leading-out port 54. A proximal end of the treatment tool inserting tube 88 is connected to a treatment tool inserting port 24f provided in the operating unit 24 in FIG. 2, and a distal end of the treatment tool inserting tube 88 is connected to a proximal end of a connecting pipe 86 (refer to FIG. 3) arranged in a connecting position between the distal end rigid portion 40 and the curved portion 42. The connecting pipe 86 is made of a stainless metal or the like and is mounted to the distal end portion body 70, and a distal end thereof is communicated with the treatment tool leading-out port 54. The treatment tool inserting tube 88 is configured by covering a tube formed of, for example, polytetrafluoroethylene having flexibility with a covering net and coating this tube with urethane or the like.

Back to FIG. 2, an ultrasonic observing unit 50, an endoscope observing unit 52 and the treatment leading-out port 54 are provided in the distal end portion body 70 (refer to FIG. 3) of the distal end rigid portion 40.

The ultrasonic observing unit 50 has an electroacoustic conversion portion provided with an observing surface for transmitting/receiving ultrasonic waves to be described later. The ultrasonic observing unit 50 obtains an ultrasonic signal that generates a tomographic image of a cellar tissue existing in a direction deeper than a body cavity wall as an ultrasonic image.

The endoscope observing unit 52 includes, as hereinafter described, components of an observation optical system and an illumination optical system, an imaging element and a peripheral circuit thereof and the like. An imaging signal displaying an endoscope image for observation is obtained by optically imaging a body cavity wall surface by the endoscope observing unit 52.

The treatment tool leading-out port 54 is, as illustrated in FIG. 3, an opening for leading out the distal end of the treatment tool (distal end 100a of the puncture needle 100 in a case of FIG. 2) composed of the puncture needle 100 and the sheath 102 inserted into the treatment tool inserting tube 88 into the inside of the body. The distal end of the connecting pipe 86 is communicated with the treatment tool leading-out port 54, and an elevator 74 is provided in the distal end side of the connecting pipe 86 to change a leading-out direction of the puncture needle 100.

The present embodiment shows the treatment tool composed of the puncture needle 100 and the sheath 102 as an example, but the treatment tool is not limited thereto, and may be the other treatment tool such as forceps.

<Operating Unit 24>

As illustrated in FIG. 2, the operating unit 24 includes an angle knob 24a that operates to bend the curved portion 42 of the insertion portion 22 to the upper-lower and the left-right, an elevation lever 24b that stands the elevator 74 (refer to FIG. 3), a suction button 24c that performs a suction operation, an air-supply/water-supply button 24d that performs an air-supply/water-supply operation, a plurality of operating members 24e that perform a display switch of the monitor, a freeze instruction or a release instruction of a display image, and the like.

The treatment tool inserting port 24f is provided to project in the distal end side of the operating unit 24 to insert various treatment tools in the treatment tool inserting tube 88 (refer to FIG. 3) therein.

The universal cord 26 has therein various signal lines that transmit electrical signals and the like, a light guide that transmits illumination light, and the like. The aforementioned various connectors 28, 30, 32 are provided in the distal end of the universal cord 26.

The ultrasonic processor unit 12 drives the electroacoustic conversion unit of the ultrasonic observing unit 50 to transmit an ultrasonic wave of a predetermined frequency to an observing target from the observing surface. The ultrasonic wave reflected from the observing target is received on the observing surface, and the received and obtained electrical signal (ultrasonic signal) is obtained from the ultrasonic observing unit 50, which is subjected to various signal processing to generate a video signal for ultrasonic image.

The endoscope processor unit 14 drives the imaging element of the endoscope observing unit 52 in the ultrasonic endoscope 10 to obtain an imaging signal transmitted from the imaging element, which is subjected to various signal processing to generate a video signal for endoscope image.

The optical source device 16 supplies the illumination light emitted from the illumination optical system of the distal end rigid portion 40 to the illumination optical system for illuminating an observation view range by the endoscope observing unit 52.

The monitor 18 receives respective video signals generated in the ultrasonic processor unit 12 and the endoscope processor unit 14 and displays an ultrasonic image and an endoscope image. The display of the ultrasonic image and the endoscope image can include a display on the monitor 18 by optionally switching only one thereof or a simultaneous display of both of the images.

<Distal End Rigid Portion 40>

FIG. 4, FIG. 5, FIG. 6 and FIG. 7 are respectively a perspective view, a plan view, a side view and a front view of the distal end rigid portion 40.

As illustrated in these drawings, the distal end portion body 70 of the distal end rigid portion 40 is provided with the ultrasonic observing unit 50, the endoscope observing unit 52 and the treatment leading-out port 54 as described above.

<Ultrasonic Observing Unit 50>

As illustrated in FIG. 3, the ultrasonic observing unit 50 has an ultrasonic vibrator 94 including an electroacoustic conversion unit 60 and a backing member 92.

The electroacoustic conversion unit 60 is composed of a plurality of piezo elements arranged along a direction of the body center axis Z of the distal end portion body 70. The plurality of piezo elements are arranged toward the proximal end side of the distal end rigid portion 40 from a position near the distal end of the distal end rigid portion 40, and an observing surface 60*a* for transmission/reception of the ultrasonic wave is formed on a surface of the electroacoustic conversion unit 60. The observing surface 60*a* is configured of an arc-shaped plane along the direction of the body center axis Z, but is not limited to this shape, and may be formed of curved planes having a plurality of different curvatures. Further, the observing surface 60*a* is provided with an acoustic lens 96 for converging ultrasonic waves along the observing surface 60*a*. The backing member 92 is fixed on the surface of the electroacoustic conversion unit 60 at the opposite side of the observing surface 60*a*.

Each of the piezo elements in the electroacoustic conversion unit 60 is provided with an unillustrated electrode, and the electrode is connected to a wire connecting portion 98 through an unillustrated flexible print board. The wire connecting portion 98 is provided on a bottom surface of the backing member 92, that is, on a bottom surface of the ultrasonic vibrator 94. A plurality of thin wires 99 are connected to the wire connecting portion 98, and the wires 99 are arranged in a wire inserting hole 71 of the distal end portion body 70 and in an unillustrated flexible pipe to be connected to the ultrasonic processor unit 12 in FIG. 2 (refer to FIG. 2).

According to the ultrasonic observing unit 50, it is possible to perform an ultrasonic electronic scan by driving each of the piezo elements in the electroacoustic conversion unit 60 in turn.

When a horizontal axis in the left-right direction vertical to the body center axis Z is indicated as "X" and a vertical axis in the upper-lower direction is indicated as "Y", the observing surface 60*a* of the electroacoustic conversion unit 60 is arranged substantially bilaterally symmetric to a plane including the body center axis Z. In the present embodiment, the piezo element is shown as an example of the electroacoustic conversion unit 60, but the electroacoustic conversion unit 60 is not limited to the piezo element, and an electrostrictive element or an ultrasonic transducer may be applied.

<Endoscope Observing Unit 52>

Figure 4:
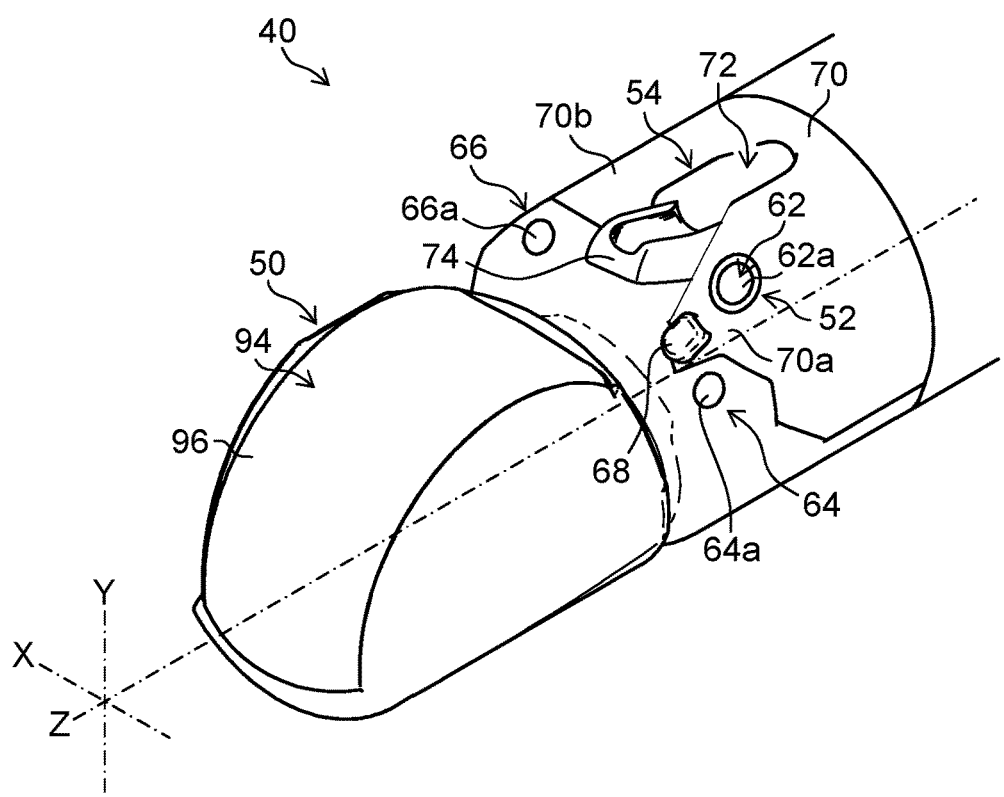
FIG. 4 is a perspective view of a distal end rigid portion of the ultrasonic endoscope.
Figure 5:
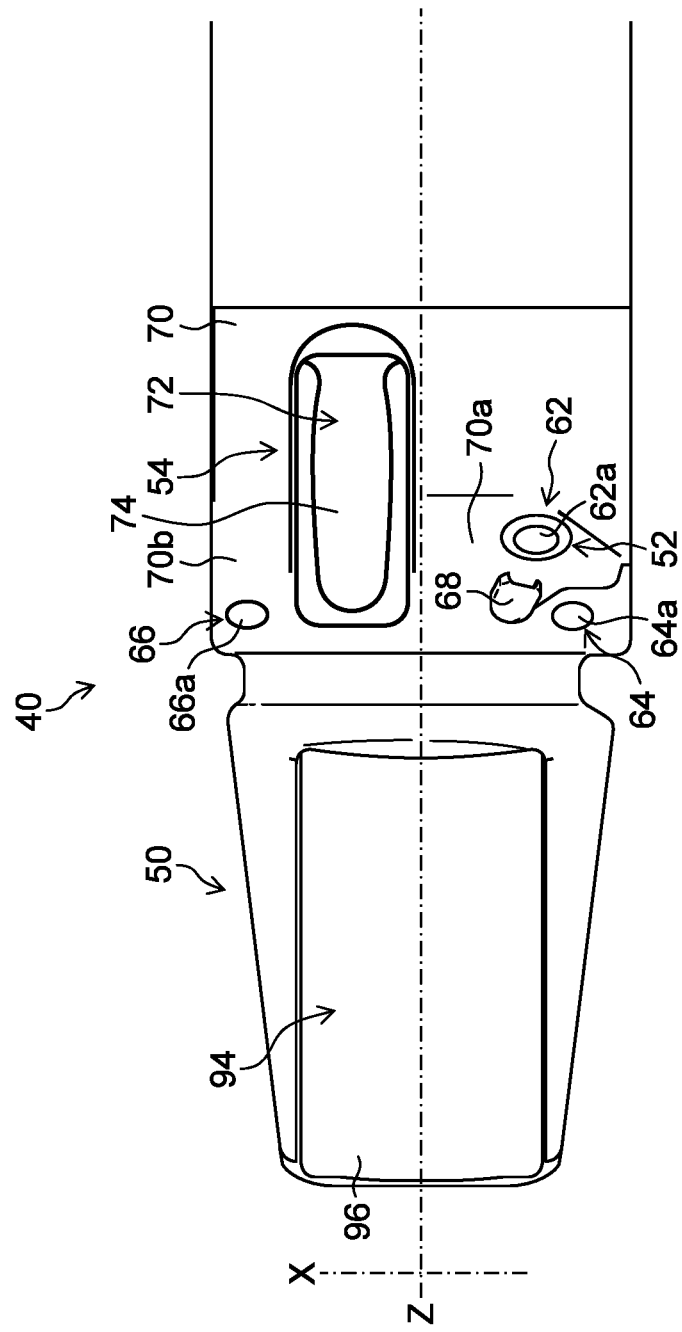
FIG. 5 is a plan view of the distal end rigid portion of the ultrasonic endoscope.
Figure 6:
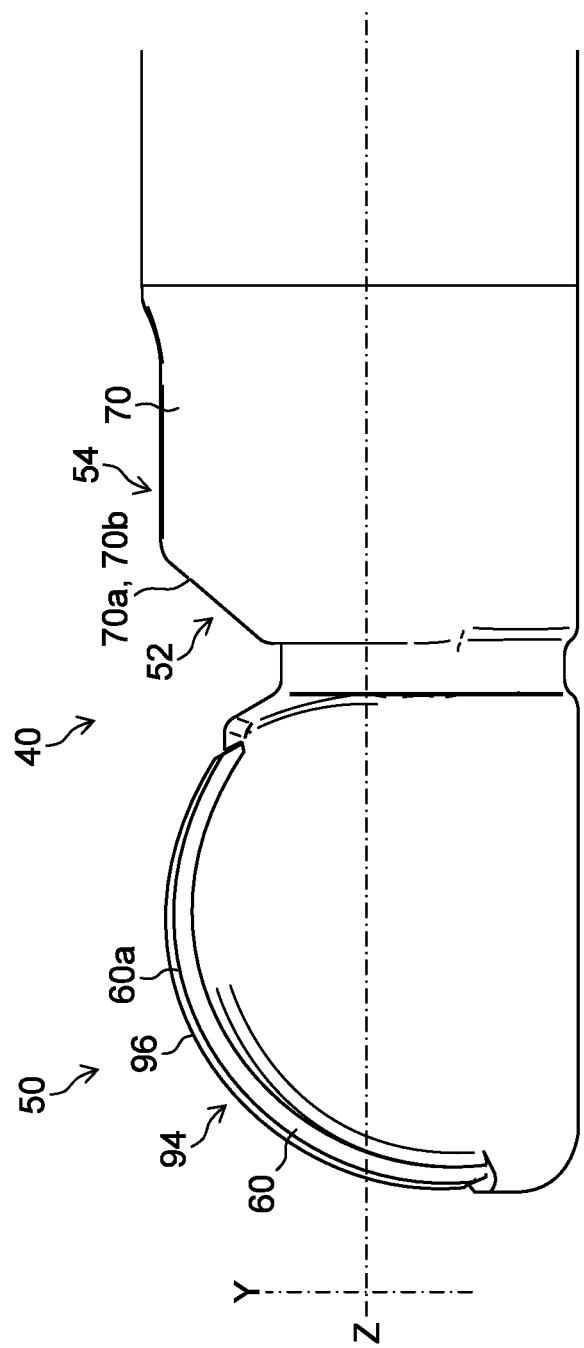
FIG. 6 is a side view of the distal end rigid portion of the ultrasonic endoscope.
Figure 7:
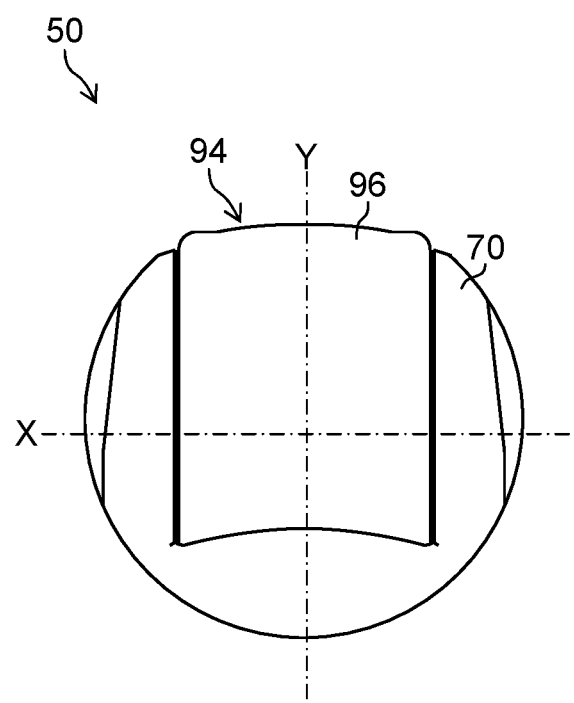
FIG. 7 is a front view of the distal end rigid portion of the ultrasonic endoscope.

As illustrated in FIG. 4 and FIG. 5, the endoscope observing unit 52 includes the observation optical system 62, the illumination optical systems 64, 66, the imaging element (unillustrated) and the like, and is arranged closer to the proximal end side than the ultrasonic observing unit 50 and in a region of the distal end portion body 70 keeping away from the treatment tool leading-out port 54.

In the distal end portion body 70, inclined surfaces 70*a*, 70*b* are provided in the distal end side and in both sides in the left-right of the treatment tool leading-out port 54 to be inclined in the proximal end side by a predetermined angle to a plane vertical to the body center axis Z. An observing window 62*a* of the observation optical system 62 and an illumination window 64*a* of one illumination optical system 64 are arranged on the left inclined surface 70*a* toward the distal end side from the proximal end side. An illumination window 66*a* of the other illumination optical system 66 is arranged on the right inclined surface 70*b* toward the distal end side from the proximal end side.

The observation optical system 62 includes an unillustrated optical system member that takes in light from an object in an observation view range from the observing window 62*a* and forms an object image inside the distal end rigid portion 40. An unillustrated imaging element is arranged inside the distal end rigid portion 40 to generate an imaging signal by taking the object image imaged by the observation optical system 62.

The illumination optical systems 64, 66 include optical system members that diffuse and emit the illumination light transmitted through the light guides from the optical source device 16 (refer to FIG. 2) in the observation view range through the illumination windows 64*a*, 66*a*.

A wash nozzle 68 is provided near the observing window 62*a* of the inclined surface 70*a* to eject liquids or gases toward the observing window 62*a*.

<Treatment Tool Leading-Out Port 54>

The treatment tool leading-out port 54 is provided closer to the proximal end side than the ultrasonic observing unit 50, and includes a recessed standing platform accommodating portion 72 communicated with an opening 86*a* of the connecting pipe 86 in FIG. 3. The elevator 74 is rotatably provided on the elevator accommodating portion 72 to change a leading-out direction of the puncture needle 100, which is led out from the opening 86*a* of the connecting pipe 86, from the treatment tool leading-out port 54.

The elevator 74 is connected to a shaft provided in an unillustrated lever. The lever is rotatably provided in the distal end portion body 70 through the shaft, and is connected to a distal end of an unillustrated operating wire, and a proximal end of the operating wire is connected to the elevation lever 24*b* (refer to FIG. 2) of the operating unit 24. Therefore when the operating wire is subjected to a push-pull operation by an operation of the elevation lever 24*b*, the elevator 74 is rotated together with the lever through the shaft to change a standing angle of the elevator 74.

As a result, the puncture needle 100 led out from the opening 86*a* of the connecting pipe 86 is guided along the elevator 74 in a predetermined leading-out direction to be led out to an exterior from the treatment tool leading-out port 54.

[Pipe Connecting Structure Between the Connecting Pipe 86 and the Treatment Tool Inserting Tube 88 in the Ultrasonic Endoscope 10]

<Connecting Method>

An explanation will be made back to FIG. 3. FIG. 3 is a cross-section surface illustrating an entire pipe connecting structure between the connecting pipe 86 and the treatment tool inserting tube 88 particularly.

For connecting the connecting pipe 86 and the treatment tool inserting tube 88, first there is a first connecting step for mounting an inner peripheral surface of the distal end of the treatment tool inserting tube 88 outward on an outer peripheral surface of the proximal end of the connecting pipe 86. Next, there is a second connecting step for mounting an inner peripheral surface of the fixing sleeve 90 outward on an outer peripheral surface of the distal end of the treatment tool inserting tube 88. That is, the pipe connecting structure of the present embodiment is configured to fix the connecting portion between the treatment tool inserting tube 88 and the connecting pipe 86 by fitting the fixing sleeve 90 outward thereon.

Here, it is preferable that the treatment tool inserting tube 88 is inserted into the fixing sleeve 90 prior to the first step. The first connecting step is executed in this insertion state, and thereafter, the fixing sleeve 90 is caused to slide in the distal end side to the treatment tool inserting tube 88 to execute the second connecting step. Thereby it is possible to smoothly execute the second connecting step.

<Fixing Sleeve 90>

Figure 8:
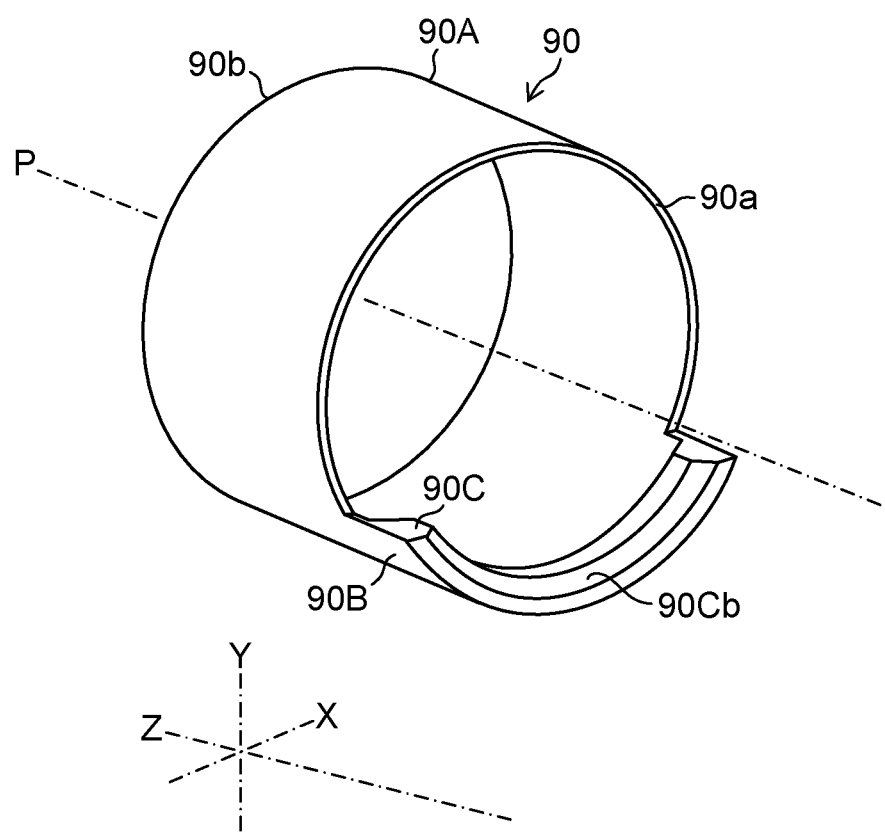
FIG. 8 is a perspective view of an entire fixing sleeve.
Figure 9A:
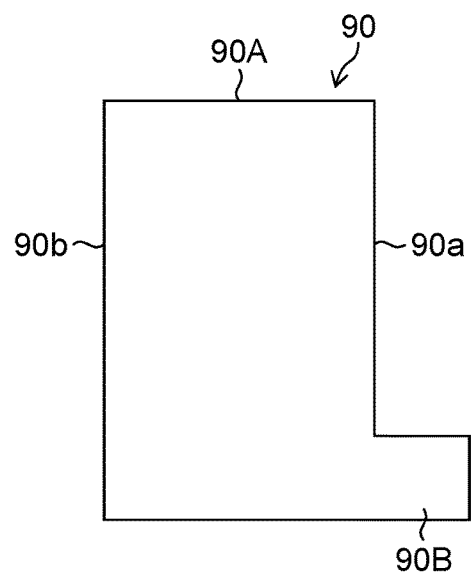
FIG. 9A is a side view of the fixing sleeve.
Figure 9B:
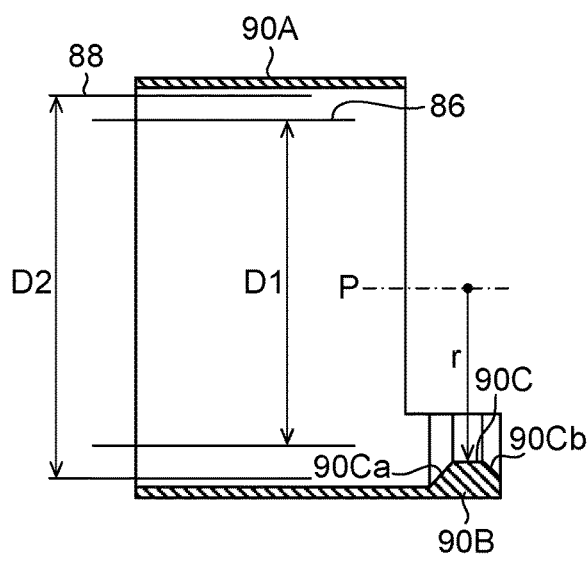
FIG. 9B is a cross section of the fixing sleeve.
Figure 9C:
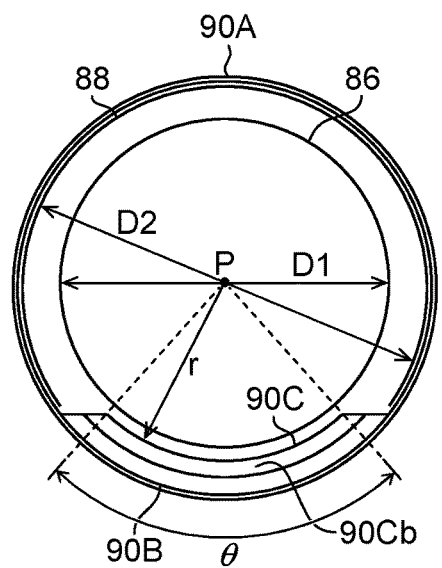
FIG. 9C is a front view of the fixing sleeve.

FIG. 8 is a perspective view of the fixing sleeve 90, and FIGS. 9A, 9B and 9C are respectively a side view, a cross section, a front view of the fixing sleeve 90.

As illustrated in these drawings, the fixing sleeve 90 includes a cylindrical sleeve body 90A having a proximal end 90a, a distal end 90b and a sleeve center axis P, an arc-shaped portion 90B along a cylindrical surface of the sleeve body 90A, and a projection portion 90C. The arc-shaped portion 90B is an arc-shaped flange connected to the proximal end side of the sleeve body 90A, and is formed in a range of the center angle θ smaller than 180° coaxially with the sleeve center axis P of the sleeve body 90A. The projection portion 90C is formed on an inner peripheral surface of the arc-shaped portion 90B in a radial inside of the sleeve center axis P along a peripheral direction of the sleeve center axis P.

The arc-shaped portion 90B of the present embodiment is formed coaxially with the sleeve center axis P of the sleeve body 90A, but may be formed coaxially with an axis slightly shifted from the sleeve center axis P. The center angle θ indicates an angle in which the arc-shaped portion 90B covers a part of the treatment tool inserting tube 88 as viewed from the axis of the arc-shaped portion 90B (same axis with the sleeve center axis P or axis slightly shifted from the sleeve center axis P). That is, the center angle θ indicates an angle in which the projection portion 90C abuts on the treatment tool inserting tube 88.

As illustrated in FIGS. 9B and 9C, the projection portion 90C is preferably configured such that, when a curvature radius of the projection portion 90C is indicated as "r" and an inner diameter of the connecting pipe 86 is indicated as "D1", "r">"D1"/2 is met. When an outer diameter of the treatment tool inserting tube 88 is indicated as "D2", it is preferable that "r"<"D2"/2 is met. The outer diameter "D2" of the treatment tool inserting tube 88 indicates an outer diameter in a state before fitting the treatment tool inserting tube 88 outward on the connecting pipe 86.

The projection portion 90C is provided with the first inclined surface 90Ca that is provided in a distal end side of the sleeve center axis P and has a normal direction including a component in a direction toward the distal end side in a direction of the sleeve center axis P and a component in a direction toward a radial inside of the sleeve center axis P.

The projection portion 90C includes the second inclined surface 90Cb that is provided in a proximal end side of the sleeve center axis P and has a normal direction including a component in a direction toward the proximal end side in a direction of the sleeve center axis P and a component in a direction toward a radial inside of the sleeve center axis P.

That is, the projection portion 90C is formed in a trapezoidal shape in a cross-section surface including the sleeve center axis P, the shape having a width smaller toward the radial inside of the sleeve center axis P. The fixing sleeve 90 is formed of, for example, a stainless material as similar to the connecting pipe 86.

<Function and Effect of the Fixing Sleeve 90>

Figure 10:
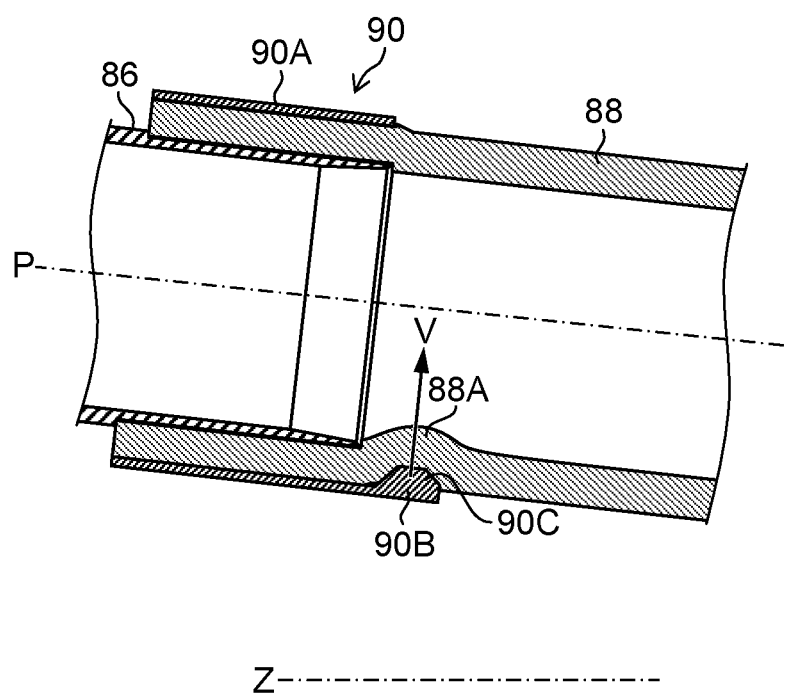
FIG. 10 is a cross section of a tube connecting structure in the non-angle form.
Figure 11:
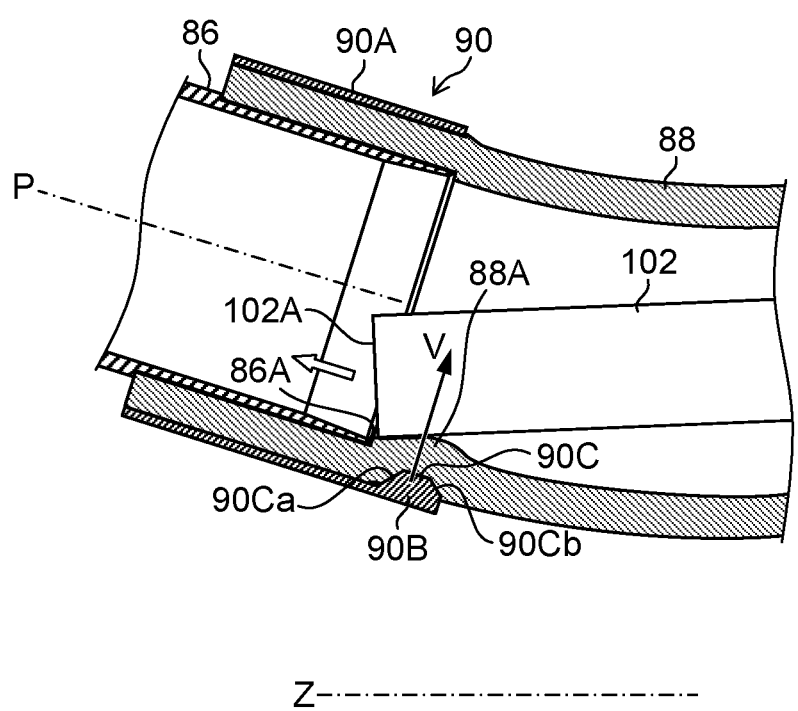
FIG. 11 is a cross section of the tube connecting structure in which a sheath is inserted in an up-angle form.

FIG. 10 is a cross section of the tube connecting structure in a non-angle form, and FIG. 11 is a cross section of the tube connecting structure in which the sheath 102 is inserted in an up-angle form.

As illustrated in FIG. 10, a part 88A of the treatment tool inserting tube 88 positioned in the connecting portion between the connecting pipe 86 and the treatment tool inserting tube 88 is pressed in the radial inside of the sleeve center axis P by the projection portion 90C formed in the arc-shaped portion 90B of the fixing sleeve 90 to be flexibly deformed in a convex shape.

Therefore a difference in level due to the inner diameter difference between the connecting pipe 86 and the treatment tool inserting tube 88 is eliminated or alleviated by the part 88A of the treatment tool inserting tube 88 flexibly deformed in the convex shape.

Even in a case of using such a fixing sleeve 90, a difference in level on an entire periphery of the connecting pipe 86 in the proximal end side is not eliminated, but a difference in level of a part of the connecting pipe 86 in which the projection portion 90C is positioned is eliminated or alleviated by the part 88A of the treatment tool inserting tube 88. In the present embodiment, a region of a part in which the difference in level is eliminated or alleviated is, as illustrated in FIG. 11, set in a region where upon inserting the sheath 102 in the up-angle form, a distal end 102A of the sheath 102 makes contact with the part 88A of the treatment tool inserting tube 88. That is, a formation position of the projection portion 90C of the fixing sleeve 90 is set not in a position in an inner peripheral portion side of the curved portion 42 curved, but in a position in an outer peripheral portion side thereof in a lateral view of the curved portion 42 in the up-angle form.

In this ultrasonic endoscope 10, even if the sheath 102 is inserted in the up-angle form and the distal end 102A of the sheath 102 abuts on the part 88A of the treatment tool inserting tube 88 flexibly deformed in the convex shape, since the part 88A is supported by the projection portion 90C of the fixing sleeve 90 to suppress the flexible deformation, the difference in level does not occur again.

Accordingly, by adopting the fixing sleeve 90 of the present embodiment, even if the sheath 102 is inserted in the up-angle form, since the distal end 102A of the sheath 102 does not knock on the proximal end 86A of the connecting pipe 86, it is possible to smoothly move forward the sheath 102 in an arrow direction in FIG. 11 from the treatment tool inserting tube 88 toward the connecting pipe 86.

In view of fitting the fixing sleeve 90 outward on the treatment tool inserting tube 88 to fix the connecting portion, it is preferable that the inner diameter of the fixing sleeve 90 is equal to or slightly larger than the outer diameter of the treatment tool inserting tube 88. The fixing sleeve 90 is provided with the projection portion 90C on the inner peripheral surface of the arc-shaped portion 90B, but the arc-shaped portion 90B is provided to be coaxial with the sleeve center axis p of the sleeve body 90A and make the center angle θ within a range smaller than 180°. Therefore the arc-shaped portion 90B does not give an influence on an effective inner diameter of the fixing sleeve 90. Since the arc-shaped portion 90B does not give the influence on the effective inner diameter of the fixing sleeve 90, it is possible to insert the treatment tool inserting tube 88 inside of the fixing sleeve 90 without deformation of the treatment tool inserting tube 88, specifically without generation of wrinkles. As a result, it is possible to secure air-tightness and water-tightness.

Further, the projection portion 90C is preferably disposed in a position close to the proximal end side of the sleeve body 90A for eliminating or alleviating the difference in level, but when the projection portion 90C is disposed too closely, the effective inner diameter of the fixing sleeve 90 is apparently smaller than the outer diameter of the treatment tool inserting tube 88 because of the presence of the projection portion 90C. For this reason, the arc-shaped portion 90B is provided to project in the proximal end side of the sleeve body 90A toward the proximal end side and the projection portion 90C is arranged in the arc-shaped portion 90B, which thus does not give an influence on the effective inner diameter of the fixing sleeve 90.

Further, the sleeve body 90A is fitted outward on the treatment tool inserting tube 88 fitted outward on the connecting pipe 86, and plays a role of fixing the treatment tool inserting tube 88 and the connecting pipe 86 such that the sleeve center axis P is in parallel with an axis of the connecting pipe 86. Accordingly a length of the sleeve body 90A in the direction of the sleeve center axis P is preferably equal to or more than at least 0.5 times an inner diameter "D" of the connecting pipe 86.

As described above, the fixing sleeve 90 is preferably configured such that when a curvature radius of the projection portion 90C is indicated as "r" and an inner diameter of the connecting pipe 86 is indicated as "D", "r">D/2 is met.

As a result, since it is possible to suppress an extension amount of the part 88A of the treatment tool inserting tube 88 flexibly deformed in the convex shape, it is possible to smoothly move forward the sheath 102 from the treatment tool inserting tube 88 toward the connecting pipe 86 without interruption of the part 88A flexibly deformed in the convex shape.

In addition, as described above, the projection portion 90C has preferably at least one inclined surface of the first inclined surface 90Ca and the second inclined surface 90Cb. Further, the projection portion 90C is preferably formed in a trapezoidal shape. Upon fixing the connecting portion between the connecting pipe 86 and the treatment tool inserting tube 88 by the fixing sleeve 90, a fixing operation of causing the fixing sleeve 90 in which the treatment tool inserting tube 88 is inserted to slide in the distal end side toward the connecting pipe 86 and pushing the treatment tool inserting tube 88 into the connecting pipe 86 by the first inclined surface 90Ca is performed. It is possible to alleviate the fixing operation force at this moment by the first inclined surface 90Ca in the distal end side of the projection portion 90C. Therefore it is possible to prevent damage of the treatment tool inserting tube 88 due to the fixing operation force of the fixing sleeve 90.

On the other hand, by providing the second inclined surface 90Cb in the proximal end side of the projection portion 90C, upon pressing the part 88A of the treatment tool inserting tube 88 by the distal end 102A of the sheath 102, the pressing force can be alleviated by the second inclined surface 90Cb. Accordingly it is possible to prevent the damage of the treatment tool inserting tube 88 due to the pressing force of the sheath 102.

As illustrated in FIG. 3, as viewed in a lateral side vertical to the body center axis Z of the distal end portion body 70, the pipe center axis P (same axis with the sleeve center axis P of the fixing sleeve 90) of the connecting pipe 86 is obliquely-crossed to the body center axis Z of the distal end portion body 70, and, as illustrated in FIG. 10 and FIG. 11, a normal direction V toward the center of the arc-shaped portion 90B preferably includes a component in a direction toward the proximal end side of the body center axis Z of the distal end portion body 70 in FIG. 3.

That is, the embodiment in FIG. 3 aims at providing the ultrasonic endoscope in the form where the pipe center axis P of the connecting pipe 86 is arranged to be obliquely-crossed to the body center axis Z of the distal end portion body 70. In this ultrasonic endoscope, the normal direction V toward the center of the arc-shaped portion 90B includes the component in the direction toward the proximal end side of the body center axis Z of the distal end portion body 70. Therefore it is possible to flexibly deform in the convex shape the part 88A of the treatment tool inserting tube 88 on which the distal end 102A of the sheath 102 inserted into the treatment tool inserting tube 88 abuts to eliminate or alleviate the difference in level due to the inner diameter difference between the connecting pipe 86 and the treatment tool inserting tube 88. Accordingly it is possible to smoothly move forward the sheath 102 toward the connecting pipe 86 from the treatment tool inserting tube 88 in the up-angle form.

Figure 12:
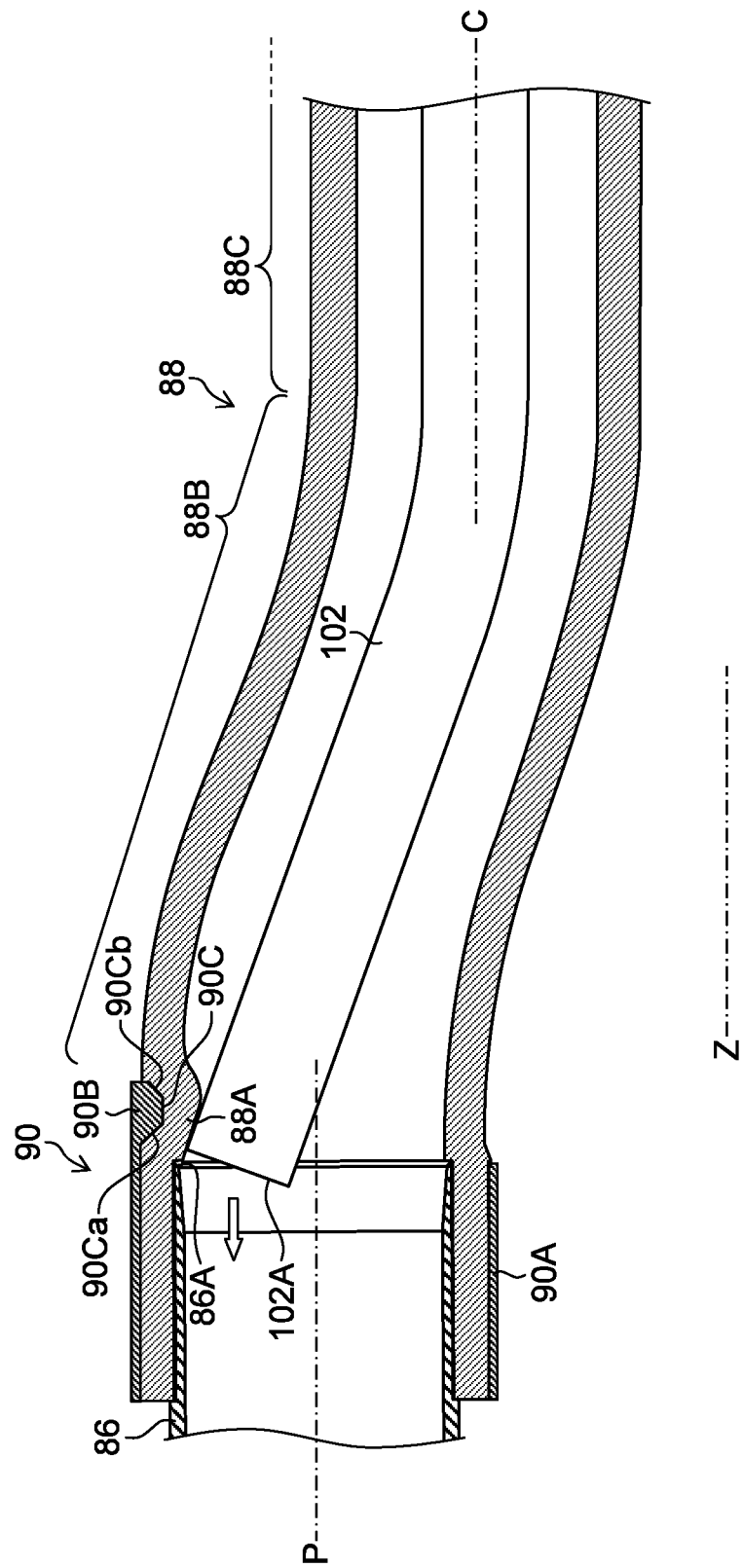
FIG. 12 is an essential-portion explaining diagram illustrating the other connecting form between the connecting pipe and the treatment tool inserting tube.

FIG. 12 is an essential-portion explaining diagram illustrating the other connecting form between the connecting pipe 86 and the treatment tool inserting tube 88.

The treatment tool inserting tube 88 includes a distal end-side tube portion 88B connected to the connecting pipe 86, and a proximal end-side tube portion 88C that is connected to a proximal end side of the distal end-side tube portion 88B and is provided in a position eccentric from the pipe center axis P of the connecting pipe 86. The arc-shaped portion 90B of the fixing sleeve 90 is preferably provided at the opposite side to a tube center axis C of the proximal end-side tube portion 88C to the pipe center axis P of the connecting pipe 86. The pipe center axis P of the connecting pipe 86 is preferably in parallel with the body center axis Z of the distal end portion body 70.

That is, the embodiment in FIG. 12 aims at providing an endoscope in the form where the tube center axis C of the proximal end-side tube portion 88C is arranged to be eccentric to the pipe center axis P of the connecting pipe 86. In this endoscope, the arc-shaped portion 90B is provided at the opposite side to the tube center axis C of the proximal end side tube portion 88C to the pipe center axis P of the connecting pipe 86. Therefore it is possible to flexibly deform in the convex shape the part 88A of the treatment tool inserting tube 88 on which the distal end 102A of the sheath 102 inserted into the distal end-side tube portion 88B abuts to eliminate or alleviate the difference in level due to the inner diameter difference between the connecting pipe 86 and the distal end-side tube portion 88B. Accordingly, it is possible to smoothly move forward the sheath 102 toward the connecting pipe 86 from the distal end-side tube portion 88B in the up-angle form.

The tube center axis C of the proximal end side tube portion 88C may be in parallel with or obliquely-crossed to the pipe center axis P of the connecting pipe 86, or may be not straight but serpentine.

Figure 13:
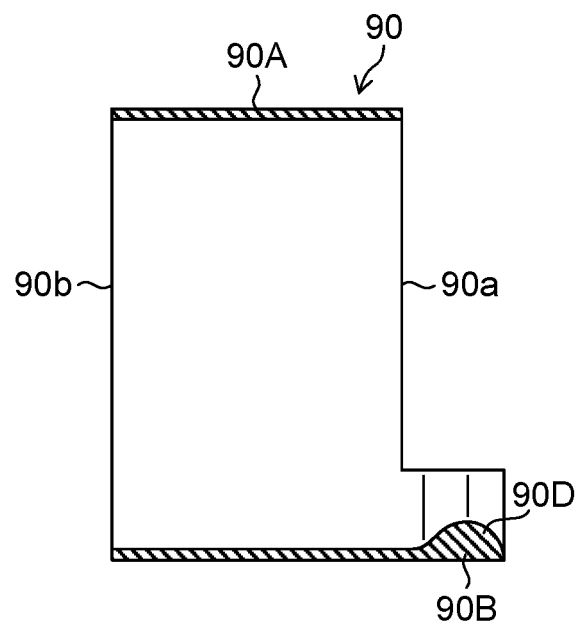
FIG. 13 is a cross section of a fixing sleeve illustrating the other form of a projection portion of the fixing sleeve.
Figure 14:
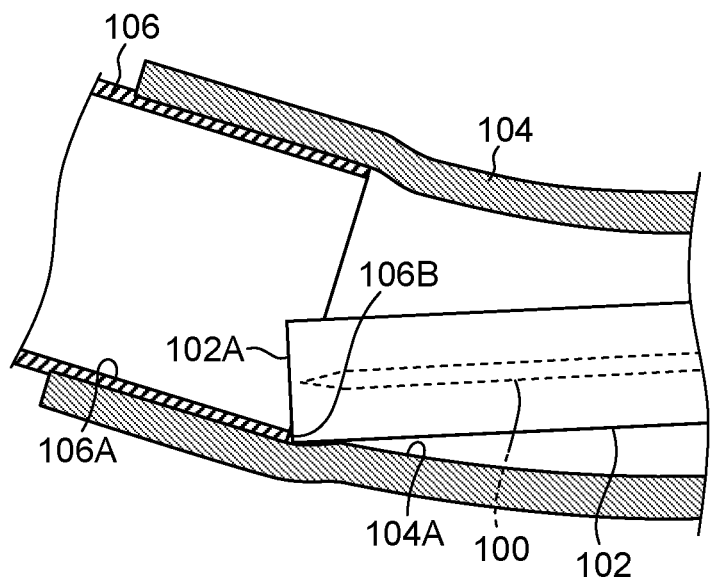
FIG. 14 is an essential-portion enlarging diagram illustrating a state where a puncture needle is inserted with a sheath in the treatment tool inserting tube in the up-angle form.
Figure 15A:
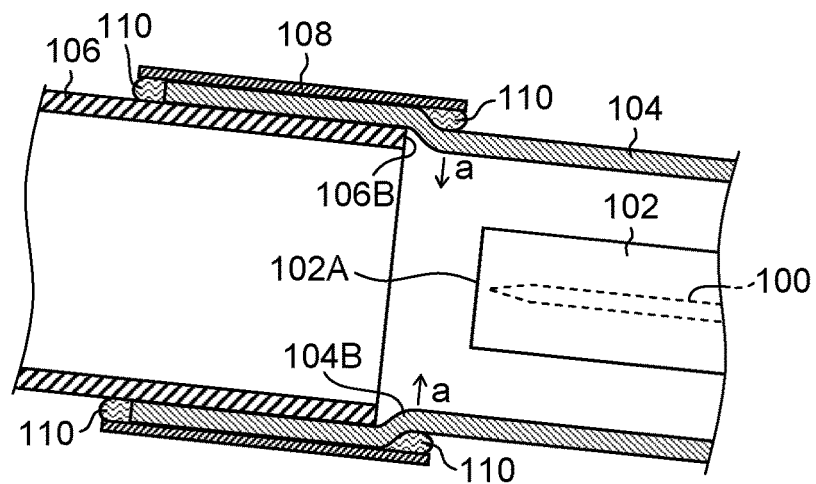
FIG. 15A is an essential-portion enlarging cross section of the non-angle form.
Figure 15B:
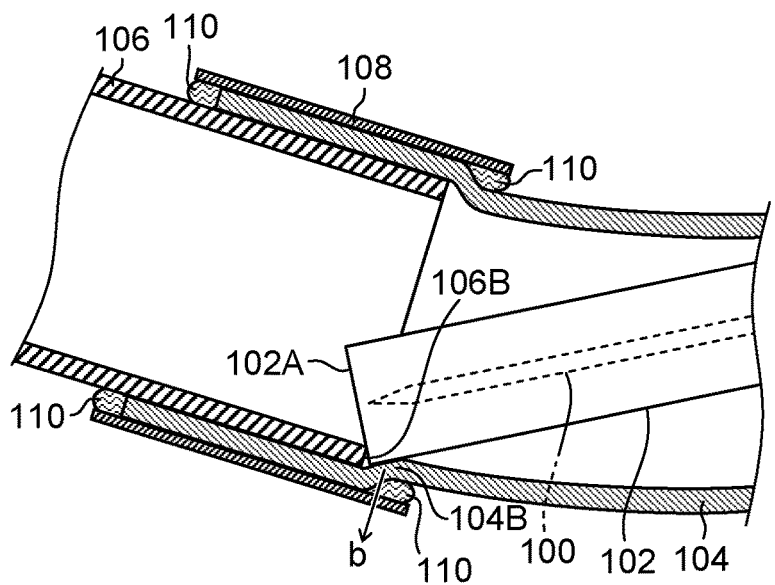
FIG. 15B is an essential-portion enlarging diagram illustrating a state where the puncture needle is inserted with the sheath in the treatment tool inserting tube in the up-angle form.

FIG. 13 is a cross section of the fixing sleeve 90 illustrating the other form of a projection portion 90D in the fixing sleeve 90. As illustrated in this drawing, even when a shape of the projection portion 90D is a curved surface shape having an edge portion without corners, it is possible to prevent damage of the treatment tool inserting tube 88 due to the fixing operation force of the fixing sleeve 90 and damage of the treatment tool inserting tube 88 due to the pressing force of the sheath 102.

What is claimed is:

1. An endoscope comprising:
   an insertion portion to be inserted into a body;
   a distal end portion body provided in a distal end of the insertion portion;
   a treatment tool leading-out port formed in the distal end portion body;
   a connecting pipe that is mounted on the distal end portion body, a distal end of which is communicated with the treatment tool leading-out port;
   a treatment tool inserting tube having flexibility that is arranged in the insertion portion, a distal end of which is connected to the connecting pipe; and
   a fixing sleeve that is fitted outward on a connecting portion between the connecting pipe and the treatment tool inserting tube for fixation of the connecting portion, wherein the fixing sleeve is one-piece part comprising:
   a cylindrical sleeve body having a distal end, a proximal end and a sleeve center axis;
   an arc-shaped portion that is connected to a proximal end of the sleeve body, is formed in an arc shape along a cylindrical surface of the sleeve body, and an extension of the entire arc-shaped portion in a circumferential direction of the sleeve center axis is smaller than a center angle of 180°; and
   a projection portion that is formed along a peripheral direction of the sleeve center axis on an inner peripheral surface of the arc-shaped portion in a radial inside of the sleeve center axis.

2. The endoscope according to claim 1, wherein the arc-shaped portion is coaxial with the sleeve center axis.

3. The endoscope according to claim 1, wherein when a curvature radius of the projection portion is indicated as "r" and an inner diameter of the connecting pipe is indicated as "D1", the following formula "r">D1/2 is met.

4. The endoscope according to claim 2, wherein when a curvature radius of the projection portion is indicated as "r" and an inner diameter of the connecting pipe is indicated as "D1", the following formula "r">D1/2 is met.

5. The endoscope according to claim 1, wherein when a curvature radius of the projection portion is indicated as "r" and an outer diameter of the treatment tool inserting tube is indicated as "D2", the following formula "r"<D2/2 is met.

6. The endoscope according to claim 2, wherein when a curvature radius of the projection portion is indicated as "r" and an outer diameter of the treatment tool inserting tube is indicated as "D2", the following formula "r"<D2/2 is met.

7. The endoscope according to claim 3, wherein when a curvature radius of the projection portion is indicated as "r" and an outer diameter of the treatment tool inserting tube is indicated as "D2", the following formula "r"<D2/2 is met.

8. The endoscope according to claim 4, wherein when a curvature radius of the projection portion is indicated as "r" and an outer diameter of the treatment tool inserting tube is indicated as "D2", the following formula "r"<D2/2 is met.

9. The endoscope according to claim 1, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

10. The endoscope according to claim 2, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

11. The endoscope according to claim 3, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

12. The endoscope according to claim 4, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

13. The endoscope according to claim 5, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

14. The endoscope according to claim 6, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

15. The endoscope according to claim 7, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

16. The endoscope according to claim 8, wherein the projection portion includes a first inclined surface that is provided in a distal end side of the sleeve center axis and has a normal direction including a component in a direction toward the distal end side in a direction of the sleeve center axis and a component in a direction toward a radial inside of the sleeve center axis.

17. The endoscope according to claim 1, wherein the projection portion includes an inclined surface that is provided in a proximal end side of the sleeve center axis and has a normal direction including a component in a direction toward the proximal end side in a direction of the sleeve center axis and a component in a direction toward a radial inside of the sleeve center axis.

18. The endoscope according to claim 1, wherein the projection portion is formed in a trapezoidal shape in a cross-section surface including the sleeve center axis, the shape having a width smaller toward a radial inside of the sleeve center axis.

19. The endoscope according to claim 1, wherein the projection portion is formed in a curved surface shape in a cross-section surface including the sleeve center axis, the shape being composed of a curved surface with an edge portion.

20. The endoscope according to claim 1, wherein, as viewed in a lateral side vertical to a body center axis of the distal end portion body, a pipe center axis of the connecting pipe is obliquely-crossed to the body center axis of the distal end portion body, and a normal direction toward the center of the arc-shaped portion includes a component in a direction toward a proximal end side of the body center axis in the distal end portion body.

21. The endoscope according to claim 1, wherein the treatment tool inserting tube includes a distal end-side tube portion connected to the connecting pipe, and a proximal end-side tube portion that is connected to a proximal end side of the distal end-side tube portion and is provided in a position eccentric from a pipe center axis of the connecting pipe, and the arc-shaped portion is provided at the opposite side to a tube center axis of the proximal end-side tube portion to the pipe center axis of the connecting pipe.

22. An endoscope comprising:

an insertion portion to be inserted into a body;

a distal end portion body provided in a distal end of the insertion portion;

a treatment tool leading-out port formed in the distal end portion body;

a connecting pipe that is mounted on the distal end portion body, a distal end of which is communicated with the treatment tool leading-out port;

a treatment tool inserting tube having flexibility that is arranged in the insertion portion, a distal end of which is connected to the connecting pipe; and a fixing sleeve that is fitted outward on a connecting portion between the connecting pipe and the treatment tool inserting tube for fixation of the connecting portion, wherein the fixing sleeve is one-piece part comprising:

a cylindrical sleeve body having a distal end, a proximal end and a sleeve center axis;

an arc-shaped portion that is formed in an arc shape along a cylindrical surface of the sleeve body and extends from a proximal end of the sleeve body, and the arc-shaped portion only exists within a center angle smaller than 180°; and a projection portion that is formed along a peripheral direction of the sleeve center axis on an inner peripheral surface of the arc-shaped portion in a radial inside of the sleeve center axis.

23. The endoscope according to claim 1, wherein an inner sidewall of the fixing sleeve extends from the sleeve body to the arc-shaped portion and has an inclined sidewall at the arc-shaped portion to form the projection portion.

24. The endoscope according to claim 22, wherein an inner sidewall of the fixing sleeve extends from the sleeve body to the arc-shaped portion and has an inclined sidewall at the arc-shaped portion to form the projection portion.

* * * * *